US008557097B2

(12) United States Patent  
Afzali-Ardakani et al.

(10) Patent No.: US 8,557,097 B2
(45) Date of Patent: Oct. 15, 2013

(54) EMBEDDING A NANOTUBE INSIDE A NANOPORE FOR DNA TRANSLOCATION

(75) Inventors: Ali Afzali-Ardakani, Ossining, NY (US); Binquan Luan, Ossining, NY (US); Hongbo Peng, Chappaqua, NY (US)

(73) Assignee: International Business Machines Corporation, Armonk, NY (US)

( * ) Notice: Subject to any disclaimer, the term of this patent is extended or adjusted under 35 U.S.C. 154(b) by 27 days.

(21) Appl. No.: 13/228,491

(22) Filed: Sep. 9, 2011

(65) Prior Publication Data

US 2013/0062212 A1 Mar. 14, 2013

(51) Int. Cl.
*G01N 27/26* (2006.01)
*C25D 17/00* (2006.01)
*B82Y 30/00* (2011.01)
*B82Y 40/00* (2011.01)

(52) U.S. Cl.
USPC ........... 204/600; 977/707; 977/712; 977/780; 977/962; 204/479; 204/450

(58) Field of Classification Search
USPC ................. 204/450, 600, 547, 479, 471, 518; 977/707, 712, 780, 962, 742, 847, 890; 216/19; 435/6.1, 7.1
See application file for complete search history.

(56) References Cited

U.S. PATENT DOCUMENTS

| | | | |
|---|---|---|---|
| 7,005,264 B2 | 2/2006 | Su et al. | |
| 7,077,939 B1 * | 7/2006 | Crooks et al. | 204/450 |
| 7,468,271 B2 | 12/2008 | Golovchenko et al. | |
| 7,625,706 B2 | 12/2009 | Akeson et al. | |
| 7,846,738 B2 | 12/2010 | Golovchenko et al. | |
| 2004/0253141 A1 * | 12/2004 | Schembri et al. | 422/58 |
| 2007/0269924 A1 * | 11/2007 | Gomez et al. | 438/99 |
| 2008/0257859 A1 * | 10/2008 | Golovchenko et al. | 216/19 |
| 2009/0321355 A1 | 12/2009 | Ratto et al. | |

FOREIGN PATENT DOCUMENTS

WO WO2010042514 A1 4/2010

OTHER PUBLICATIONS

Kurashima et al. (Microelectronic Engineering 87, Nov. 2009, 1516-1518).*
Holt, et al., "Fast Mass Transport Through Sub-2 Nanometer Carbon Nanotubes", Science, vol. 312; 2006, pp. 1034-1037.
Kasianowicz, et al., "Characterization of Individual Polynucleotide Molecules Using a Membrane Channel", Proc. Natl. Acad. Sci.; USA. vol. 93, 1996; pp. 13770-13773.

(Continued)

*Primary Examiner* — J. Christopher Ball
*Assistant Examiner* — Jennifer Dieterle
(74) *Attorney, Agent, or Firm* — Cantor Colburn LLP; Vazken Alexanian (57) ABSTRACT

A technique for embedding a nanotube in a nanopore is provided. A membrane separates a reservoir into a first reservoir part and a second reservoir part, and the nanopore is formed through the membrane for connecting the first and second reservoir parts. An ionic fluid fills the nanopore, the first reservoir part, and the second reservoir part. A first electrode is dipped in the first reservoir part, and a second electrode is dipped in the second reservoir part. Driving the nanotube into the nanopore causes an inner surface of the nanopore to form a covalent bond to an outer surface of the nanotube via an organic coating so that the inner surface of the nanotube will be the new nanopore with a super smooth surface for studying bio-molecules while they translocate through the nanotube.

16 Claims, 8 Drawing Sheets

(56) References Cited

OTHER PUBLICATIONS

King, et al., "Probing Nanotube-Nanopore Interactions", Phys. Rev. Lett., vol. 95, 2005. pp. 216103-(1-4); 4 pages.

Liu, et al., "Translocation of Single-Stranded DNA Through Single-Walled Carbon Nanotubes", Science; vol. 327, o. 5961; Jan. 1, 2010; pp. 64-67.

Lulevich, et al., "Frictionless Sliding of Single-Stranded DNA in a Carbon Nanotube Pore Observed by Single Molecule Force Spectroscopy", Nano Lett., vol. 11, No. 3, 2011; (Web Publication Jan. 28, 2011), pp. 1171-1176.

Xiu, et al., "Manipulating Biomolecules with Aqueous Liquids Confined within Single-Walled Nanotubes", J. Am. Chem. Soc.; vol. 131; No. 8; 2009; pp. 2840-2845.

Yeh, et al., "Nucleic Acid Transport Through Carbon Nanotube Membranes", Proc. Natl. Acad. Sci.; USA; vol. 101; No. 33; Aug. 17, 2004; pp. 12177-12182.

\* cited by examiner

EMBEDDING A NANOTUBE INSIDE A NANOPORE FOR DNA TRANSLOCATION

BACKGROUND

Exemplary embodiments relate to nanodevices, and more specifically, to providing a smooth inner surface for a nanopore by fixing a nanotube inside the nanopore.

Recently, there has been growing interest in applying nanopores as sensors for rapid analysis of biomolecules (e.g., polymers) such as deoxyribonucleic acid (DNA), ribonucleic acid (RNA), protein, etc. Emphasis has been given to applications of nanopores for DNA sequencing, as this technology holds the promise to reduce the cost of sequencing below $1000/human genome.

Nanopore sequencing is a technique for determining the order in which nucleotides occur on a strand of DNA. A nanopore is simply a small hole of the order of several nanometers in internal diameter. The theory behind nanopore sequencing has to do with what occurs when the nanopore is immersed in a conducting fluid and an electric potential (voltage) is applied across it: under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be put around the nanopore so that DNA bases can be differentiated while the DNA passes through the nanopore.

BRIEF SUMMARY

According to an exemplary embodiment, an apparatus for embedding a nanotube in a nanopore is provided. The apparatus includes a membrane separating a reservoir into a first reservoir part and a second reservoir part, and the nanopore is formed through the membrane for connecting the first and second reservoir parts. An ionic fluid fills the nanopore, the first reservoir part, and the second reservoir part. A first electrode is dipped in the first reservoir part, and a second electrode is dipped in the second reservoir part. A voltage bias is applied to the first and second electrodes to drive the nanotube into the nanopore so that the inner surface of the nanopore forms a covalent bond to an outer surface of the nanotube via an organic coating According to an exemplary embodiment, a system for embedding a nanotube in a nanopore is provided. The system includes an apparatus including a membrane separating a reservoir into a first reservoir part and a second reservoir part, where the nanopore is formed through the membrane for connecting the first and second reservoir parts. An ionic fluid fills the nanopore, the first reservoir part, and the second reservoir part. A first electrode is dipped in the first reservoir part, and a second electrode is dipped in the second reservoir part. Also, the system includes a voltage source configured to drive the nanotube into the nanopore in order to cause an inner surface of the nanopore to form a covalent bond to an outer surface of the nanotube via an organic coating.

According to an exemplary embodiment, an apparatus is provided for embedding a nanotube in a nanopore. The apparatus includes a membrane separating a reservoir into a first reservoir part and a second reservoir part, and the nanopore is formed through the membrane for connecting the first and second reservoir parts. An ionic fluid fills the nanopore, the first reservoir part, and the second reservoir part. A first electrode is dipped in the first reservoir part, and a second electrode is dipped in the second reservoir part. The nanotube is driven into the nanopore by a difference in fluidic pressure on two sides of the membrane, which causes an inner surface of the nanopore to form a covalent bond to an outer surface of the nanotube via an organic coating.

Additional features are realized through the techniques of the present disclosure. Other systems, methods, apparatus, and/or computer program products according to other embodiments are described in detail herein and are considered a part of the claimed invention. For a better understanding of exemplary embodiments and features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The foregoing and other features of the present disclosure are apparent from the following detailed description taken in conjunction with the accompanying drawings in which:

DETAILED DESCRIPTION

An issue in DNA sequencing is to control the translocation of the DNA through the nanopore. The surface roughness of the nanopore and the dangling bonds on the surface of the nanopore may present problems for DNA sequencing. After drilling a solid-state nanopore using an electron beam, the pore surface may exhibit nanometer scale corrugations (e.g., folds, wrinkles, groves, etc.). Similar to the scaling behavior of a self-affine rough surface, the smaller a nanopore is the rougher the inner pore surface is. Additionally, nanopores drilled using the same procedure may have different surface roughness, causing each pore to be unique. Thus, experiments that are performed using nanopores with rough surfaces and/or dangling bonds may likely (or may possibly) show inconsistent results because of the unpredictable interactions between DNA and the inner surface of the nanopore. For example, simulations show that the effective electric driving forces on DNA are different if the surface roughness of the same-sized nanopores is different.

Exemplary embodiments are configured to attach carbon nanotubes at the inner surface of the nanopore and leverage the smoothness of the inner surface of carbon nanotubes. This approach can eliminate the physical surface roughness as well as the dangling bonds at the inner surface of the nanopore, which are the sources of unpredictable interactions between DNA and the inner surface of the nanopore. Additionally, the chemical inertness of carbon nanotubes will be a potential benefit, such as by protecting the metal electrodes employed at the inner surface of the nanopore.

Figure 1:
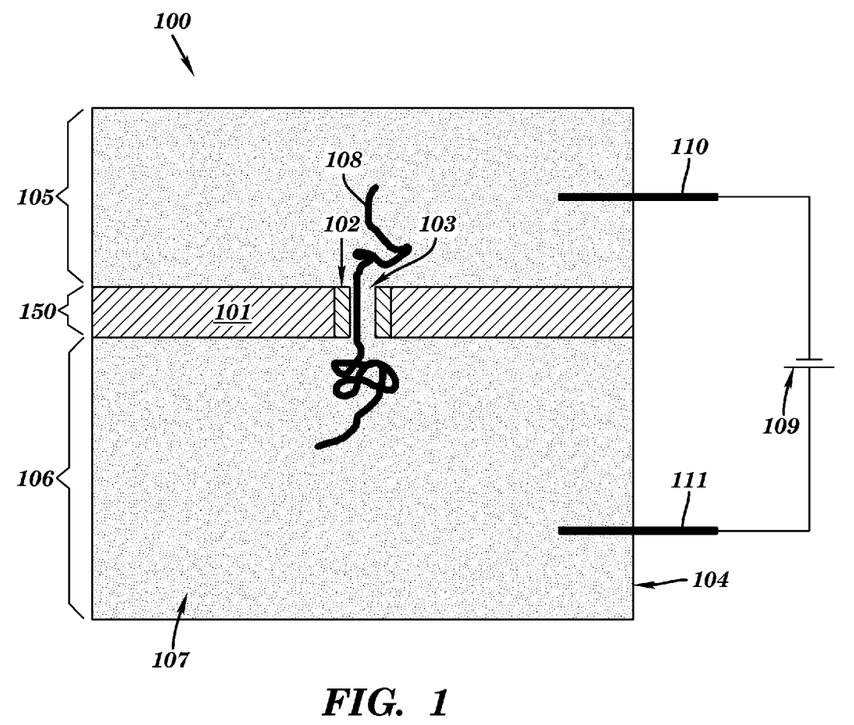
FIG. 1 depicts a cross-sectional schematic of a nanodevice with a nanopore embedded with a carbon nanotube according to an exemplary embodiment.

Now turning to the figures, FIG. 1 depicts a cross-sectional schematic of a nanodevice 100 with a nanopore embedded with a carbon nanotube according to an exemplary embodiment. The nanodevice 100 illustrates a DNA translocation setup. A membrane 150 is made of one or more insulating films 101 with a nanopore 103 formed through the insulating film 101. A carbon nanotube 102 is embedded at the inner surface of the nanopore 103. The insulating film 101 of the membrane 150 partitions a reservoir 104 into two reservoir parts, which are reservoir part 105 and reservoir part 106. The reservoir 104 (including reservoir parts 105 and 106) and the nanopore 103 are then filled with ionic buffer/fluid 107 (e.g., such as a conductive fluid).

A polymer 108 such as a DNA molecule(s) is loaded into the nanopore 103 by an electrical voltage bias of the voltage source 109, which is applied across the nanopore 103 via two electrochemical electrodes 110 and 111. The electrodes 110 and 111 are respectively dipped in the ionic buffer 107 of the reservoir part 105 and the reservoir part 106 in the reservoir 104.

There are various state of the art techniques for sensing DNA bases and controlling the motion of the DNA, and the roughness and the dangling bonds in a regular (state of the art) nanopore may pose a potential problem. However, the smooth inner surface of the nanotube 102 will provide a (very) smooth surface with no dangling bonds for characterization (i.e., nanopore sequencing of the DNA) and movement of the polymer 108.

Figure 2A:
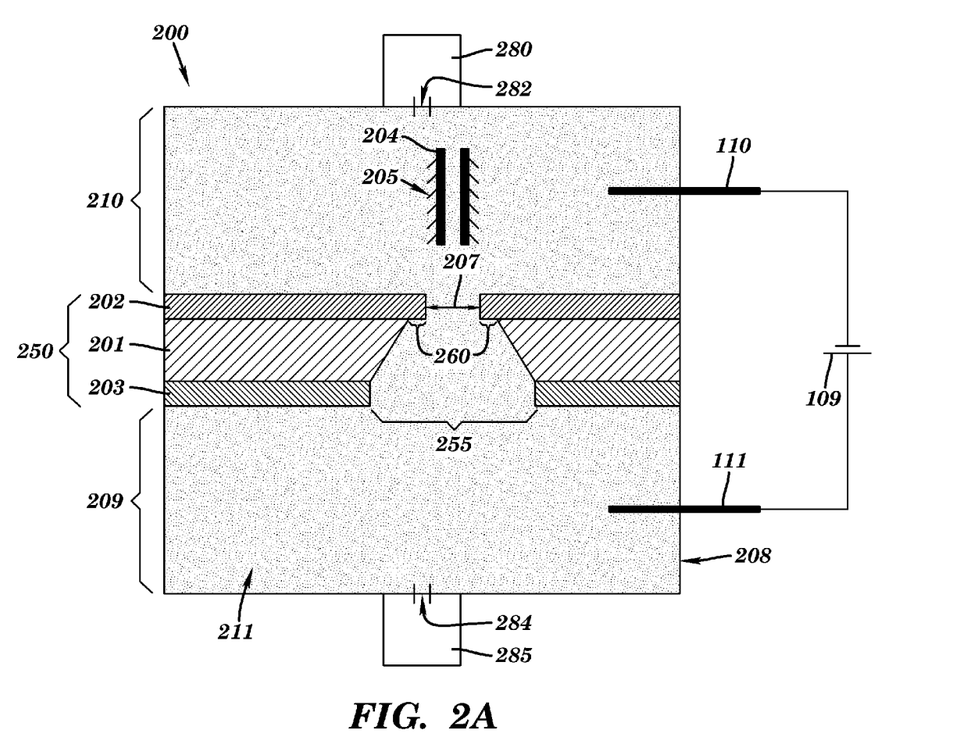
FIG. 2A illustrates an approach to embed a carbon nanotube inside a nanopore of a nanodevice according to an exemplary embodiment.
Figure 2B:
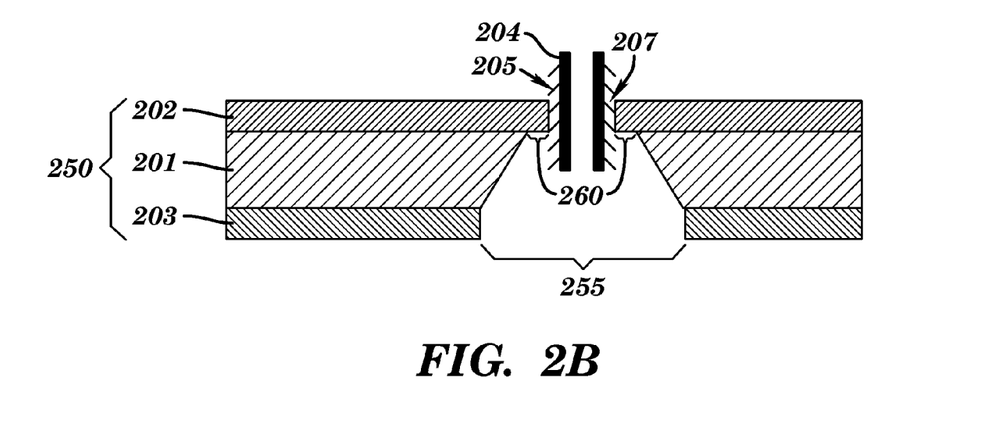
FIG. 2B illustrates the carbon nanotube attached/bonded to the inside of the nanopore according to an exemplary embodiment.
Figure 2C:
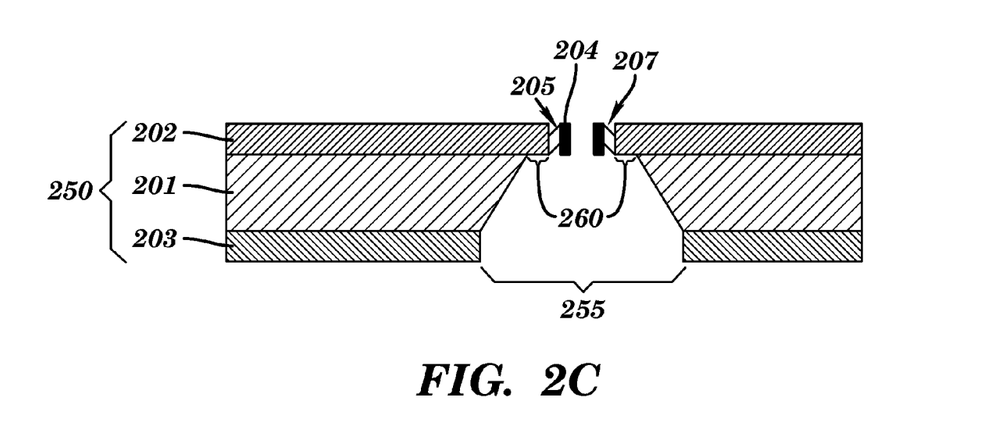
FIG. 2C illustrates the carbon nanotube attached to the inside of the nanopore after processing according to an exemplary embodiment.

There may be many techniques with many different materials that can be utilized to make the nanodevice 100 shown in FIG. 1. According to an exemplary embodiment, FIGS. 2A, 2B, and 2C illustrate one approach to embed a carbon nanotube inside a nanopore of a nanodevice 200 such as a chip. FIGS. 2A, 2B, and 2C depict a cross-sectional schematic of the nanodevice 200. In FIG. 2A, a membrane 250 includes a substrate 201 (e.g., such as silicon), between membrane parts 202 and 203. The membrane parts 202 and 203 may be made of a material (such as $Si_3N_4$ (silicon nitride)) with a high etching selectivity with respect to the substrate 201. The membrane part 202 may also contain other material layers, such as metal layers, etc., for any desired application. A window 255 is opened into the membrane part 203 using, e.g., reactive ion etching, and the substrate 201 will be etched through to the membrane part 202; etching through the window 255 of the membrane part 203 as well as through the substrate 201 will form a free-standing membrane part 260 of the membrane part 202. In the case of a silicon substrate for the substrate 201, the etchant could be KOH (potassium hydroxide) or TMAH (tetramethylammonium hydroxide) at 80° C. A nanopore 207 is made/formed through the free-standing membrane part 260 of the membrane part 202. The membrane 250 (including the free-standing membrane part 260) partitions a reservoir 208 into reservoir part 209 and reservoir part 210. The reservoir 208 (including reservoir parts 209 and 210) and the nanopore 207 formed through membrane part 202 are (then) filled with ionic buffer/fluid 211. The nanopore 207 is a small aperture formed in, e.g., the free-standing membrane part 260 of the membrane part 202.

As shown in FIG. 2A, the outer surface of a carbon nanotube 204 can be coated with an organic coating 205. The organic coating 205 is configured to be covalently bonded to the inner surface of the nanopore 207. The organic coating 205 and/or the carbon nanotube 204 is charged (by tuning the pH of the ionic buffer 211), such that the carbon nanotube 204 can be transported/driven into the nanopore 207 by the voltage source 109 applying a voltage bias to electrodes 110 and 111, and then the carbon nanotube 204 can be covalently bonded to the inner surface of the nanopore 207, as shown in FIG. 2B. Alternatively and/or additionally, a fluidic pressure adjustment device 280 can be communicatively connected to the reservoir part 210 via a port 282, and a fluidic pressure adjustment device 285 can be communicatively connected to the reservoir part 209 via another port 284 in one implementation. To drive the carbon nanotube 204 (which can be charged or uncharged) into the nanopore 207, the fluidic pressure adjustment device 280 is configured to apply a positive fluidic pressure to the reservoir part 210 and/or the fluidic pressure adjustment device 285 is configured to apply a negative fluidic pressure to the reservoir part 209. The carbon nanotube 204 is driven into the nanopore 207 by the difference in fluidic pressure on both sides of the membrane 250 caused by fluidic pressure adjustment device 280 and 285. Also, the carbon nanotube 204 can be driven into the nanopore 207 by the positive fluidic pressure of the fluidic pressure adjustment device 280 alone or by the negative fluidic pressure of the fluidic pressure adjustment device 285 alone. The fluidic pressure adjustment devices 280 and 285 may be pumps or syringes respectively linked via ports 282 and 284 to the reservoir parts 210 and 209 to apply the desired pressure.

The ionic buffer 107 and 211 in the reservoirs 104 and 208 can be any salt dissolved in any solvent (water or organic solvent) with any pH depending on the application. One example of the ionic buffer 107 and 211 includes a KCl (potassium chloride) solution in water with a pH range from 6-9 for DNA translocation. Accordingly, the electrodes 110 and 111 can be any electrodes for electrochemical reactions that match the salt and solvent. For example, Ag/AgCl electrodes can be a good match for the KCl solution in water.

As discussed further below, the organic coating 205 is a material having chemical properties that cause the organic coating 205 (applied to the carbon nanotube 204) to covalently bond to the inner surface material of the nanopore 207. As a result of the covalent bond, the carbon nanotube 204 is securely attached to the nanopore 207.

Once the carbon nanotube 204 is attached to the inner surface of nanopore 207, both sides (e.g., top and bottom) of the membrane 250 (including the attached nanotube 204) can be processed/etched with $O_2$ (oxygen) plasma to tailor (e.g., remove) the parts of the carbon nanotube 204 that are extending outside of the nanopore 207, as shown in FIG. 2C. In FIG. 2C, the height of the carbon nanotube 204 (e.g., the top and bottom) is aligned with the height of the membrane part 202 after the $O_2$ plasma processing. The polymer 108 (shown in FIG. 1) may be driven into the carbon nanotube 204 attached to the nanopore 207 for sequencing by a nanopore sequencer (not shown), and the sequencing occurs in the nanopore 207 (formed by the carbon nanotube 204) as understood by one skilled in the art.

Oxygen plasma etching is a form of plasma processing used to fabricate integrated circuits. As understood by one skilled in the art, it involves a high-speed stream of glow discharge (plasma) of an appropriate gas mixture being shot (in pulses) at a sample, such as at the membrane 250. Although plasma etching is described, it is contemplated that other types of etching may be utilized as understood by one skilled in the art.

Figure 3A:
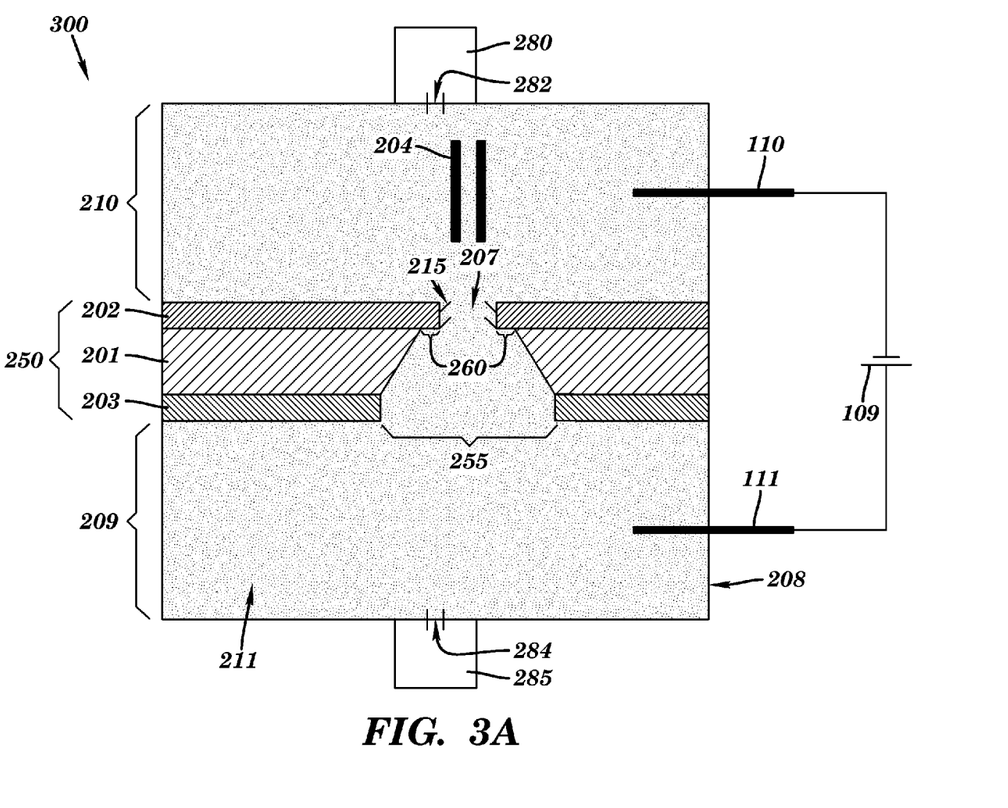
FIG. 3A illustrates another approach to embed a carbon nanotube inside a nanopore of a nanodevice according to an exemplary embodiment.
Figure 3B:
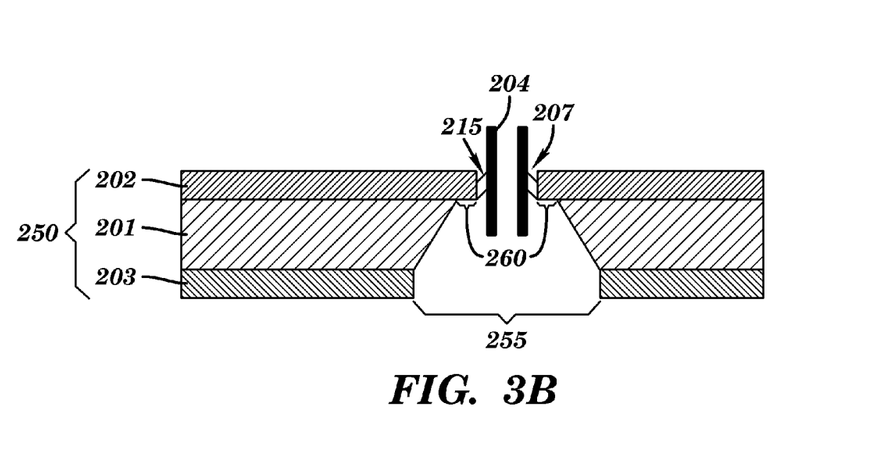
FIG. 3B illustrates the carbon nanotube attached/bonded to the inside of the nanopore according to an exemplary embodiment.
Figure 3C:
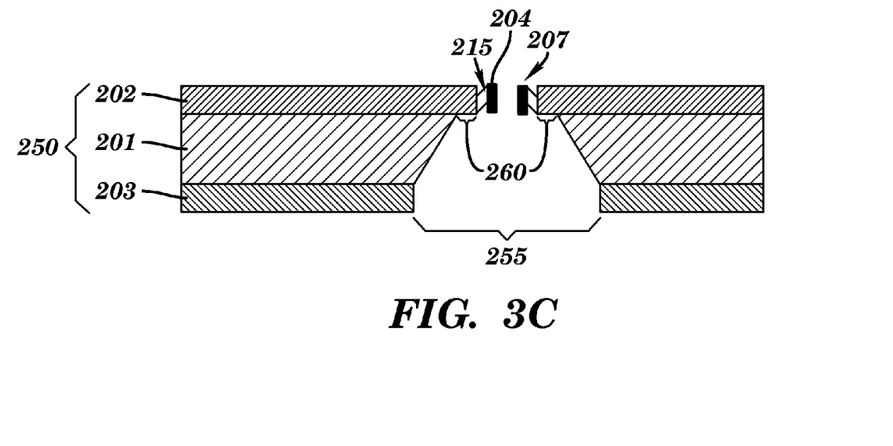
FIG. 3C illustrates the carbon nanotube attached to the inside of the nanopore after processing according to an exemplary embodiment.

FIGS. 3A, 3B, and 3C illustrate another approach to embed a carbon nanotube inside a nanopore according to an exemplary embodiment. FIGS. 3A, 3B, and 3C depict a cross-sectional schematic of the nanodevice 300.

In FIGS. 3A, 3B, and 3C, the inner surface of the nanopore 207 is coated with the organic coating 215, which can bond to the carbon nanotube 204. The description for FIGS. 3A, 3B, and 3C are the same as for FIGS. 2A, 2B, and 2C, except that the carbon nanotube 204 is initially uncoated because the coating is applied to the inner surface of the nanopore 207, instead of on the carbon nanotube 204 (itself). The organic coating 215 in FIGS. 3A, 3B, and 3C may be the same material as the organic coating 205 in FIGS. 2A, 2B, and 2C in one implementation, and may be different materials in another implementation.

In FIG. 3A, the membrane 250 includes the substrate 201, between membrane parts 202 and 203, and window 255 is opened/etched into the membrane part 203 through the substrate 201 to the membrane part 202 to form the free-standing membrane part 260 of the membrane part 202, as discussed above. The nanopore 207 is made/formed through the free-standing membrane part 260. The membrane 250 (including the free-standing membrane part 260) partitions a reservoir 208 into reservoir part 209 and reservoir part 210. The reservoir 208 (including reservoir parts 209 and 210) and the nanopore 207 formed through membrane part 202 are then filled with ionic buffer/fluid 211 as discussed above.

Unlike FIG. 2A, the outer surface of the carbon nanotube 204 is not coated with the organic coating 205 in FIG. 3A. Instead, the inner surface of the nanopore 207 is coated with the organic coating 215. The organic coating 215 is configured to covalently bond to the outer surface of the uncoated carbon nanotube 204. If the carbon nanotube 204 is charged (by tuning the pH of the ionic buffer 211 filling the reservoir 208), the carbon nanotube 204 can be transported into the nanopore 207 by a voltage bias applied to electrodes 110 and 110 via the voltage source 109. Also, the carbon nanotube 204 can be driven into the nanopore 207 by the difference in fluidic pressure on both sides of the membrane 250 applied by positive and negative pressures of the fluidic pressure adjustment devices 280 and 285. Once the carbon nanotube 204 is driven into the nanopore 207, the carbon nanotube 204 can be covalently bonded to the inner surface of the nanopore 207 via the organic coating 215, as shown in FIG. 3B. The organic coating 215 is a material having chemical properties that cause the organic coating 215 (applied to the nanopore 207) to covalently bond to the outer surface material of the uncoated carbon nanotube 204. As a result of this covalent bond, the carbon nanotube 204 is securely attached to the nanopore 207.

Once the carbon nanotube 204 is attached to the inner surface of nanopore 207, both sides of the membrane 250 (including the attached nanotube 204) can be processed with $O_2$ plasma to tailor (e.g., remove) the extending parts of the carbon nanotube 204 that extend outside of the nanopore 207, as shown in FIG. 3C. In FIG. 3C, the height of the carbon nanotube 204 is aligned to the height of the membrane part 202 after $O_2$ plasma processing. The polymer 108 (shown in FIG. 1) may be driven into the carbon nanotube 204 attached to the nanopore 207 for sequencing as understood by one skilled in the art.

Figure 4A:
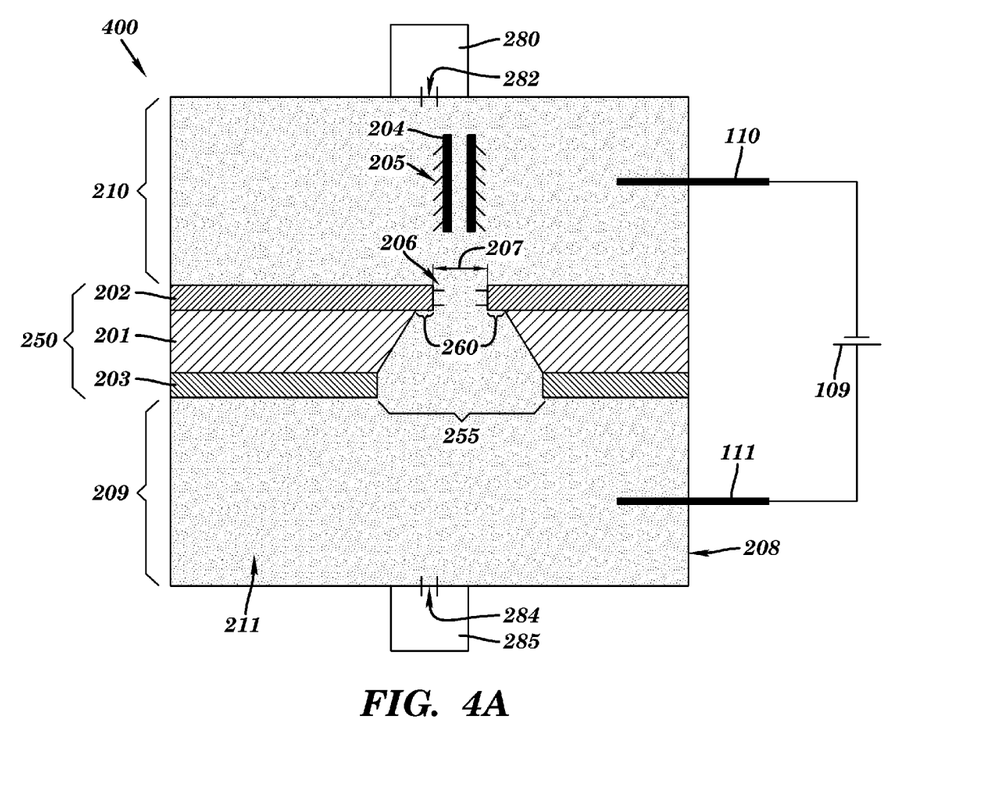
FIG. 4A illustrates an additional approach to embed a carbon nanotube inside a nanopore of a nanodevice according to an exemplary embodiment.
Figure 4B:
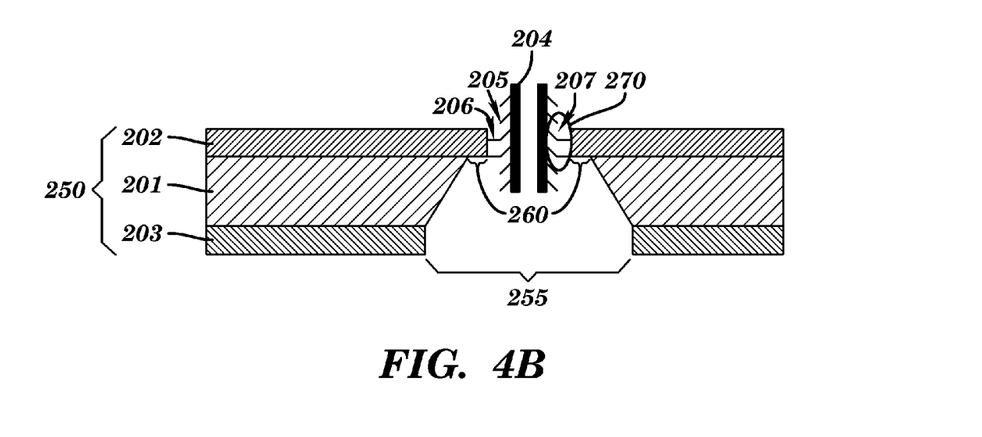
FIG. 4B illustrates the carbon nanotube attached/bonded to the inside of the nanopore according to an exemplary embodiment.
Figure 4C:
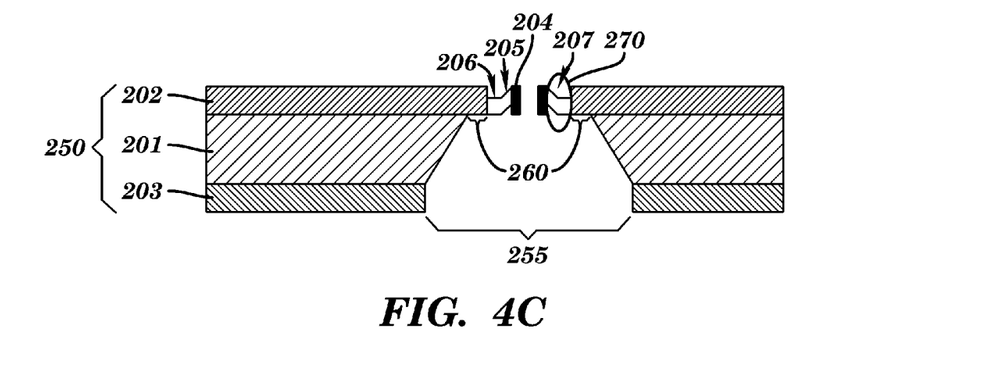
FIG. 4C illustrates the carbon nanotube attached to the inside of the nanopore after processing according to an exemplary embodiment.

FIGS. 4A, 4B, and 4C illustrate an additional approach to embed a carbon nanotube inside a nanopore according to an exemplary embodiment. FIGS. 4A, 4B, and 4C depict a cross-sectional schematic of the nanodevice 400 which illustrates a combination of the approaches discussed in FIGS. 2A, 2B, 2C, 3A, 3B, and 3C.

In FIGS. 4A, 4B, and 4C, the inner surface of the nanopore 207 is coated with an organic coating 206, while the outer surface of the carbon nanotube 204 is coated with the organic coating 205. The organic coating 205 is chemically configured to covalently bond to the organic coating 206. Additionally, the organic coating 205 is chemically configured to bond to the carbon nanotube 204, and the organic coating 206 is chemically configured to bond to the inner surface of the nanopore 207. The organic coating 205 is different from the organic coating 206 in one implementation. In another implementation, the organic coating 205 can be the same material as the organic coating 206.

When the organic coating 205 and/or carbon nanotube 204 is charged (by tuning the pH of the ionic buffer), the carbon nanotube 204 can be transported into the nanopore 207 by a voltage bias applied to electrodes 110 and 110 via the voltage source 109. Also, the carbon nanotube 204 can be driven into the nanopore 207 by the difference in fluidic pressure on both sides of the membrane 250 applied by the positive and negative pressures of the fluidic pressure adjustment devices 280 and 285. Once the carbon nanotube 204 coated in the organic coating 205 is driven into the nanopore 207 coated in the organic coating 206, the carbon nanotube 204 can be covalently bonded to the inner surface of the nanopore 207 via the organic coatings 205 206, as shown in FIG. 4B. The organic coating 205 is a material having chemical properties that cause the organic coating 205 (applied to the carbon nanotube 204) to covalently bond to the outer surface material of the carbon nanotube 204 and to the organic coating 206. Similarly, the organic coating 206 is a material having chemical properties that cause the organic coating 206 (applied to the nanopore 207) to covalently bond to the outer surface material of the carbon nanotube 204 and to the organic coating 205. As a result of the covalent bonding, the carbon nanotube 204 is securely attached to the nanopore 207.

As mentioned above, once the carbon nanotube 204 is attached to the inner surface of nanopore 207, both sides of the membrane 250 (including the attached nanotube 204) can be processed with $O_2$ plasma to tailor (e.g., remove) the extending parts of the carbon nanotube 204 that extend outside of the nanopore 207, as shown in FIG. 4C. In FIG. 4C, the height of the carbon nanotube 204 is aligned to the height of the membrane part 202 after $O_2$ plasma processing. In one implementation, the height of the carbon nanotube 204 may be slightly less than, more than, or about the same as the height of the membrane part 202 (forming the nanopore 207) based on the desired precision of the $O_2$ plasma processing. The polymer 108 (shown in FIG. 1) may be driven into the carbon nanotube 204 attached to the nanopore 207 for sequencing as understood by one skilled in the art.

Although exemplary embodiments described above may be directed to carbon nanotubes, it should be appreciated that the disclosure is not restricted to nanopores with carbon nanotubes. Rather, exemplary embodiments may be applicable for attaching other types of nanotubes to the inside surface of nanopores utilizing the techniques as discussed herein. Additionally, exemplary embodiments are not limited to embedding nanotubes into nanopores, and nanotubes may be embedded into other structures such as vias, nanochannels, etc., as understood by one skilled in the art.

Figure 5:
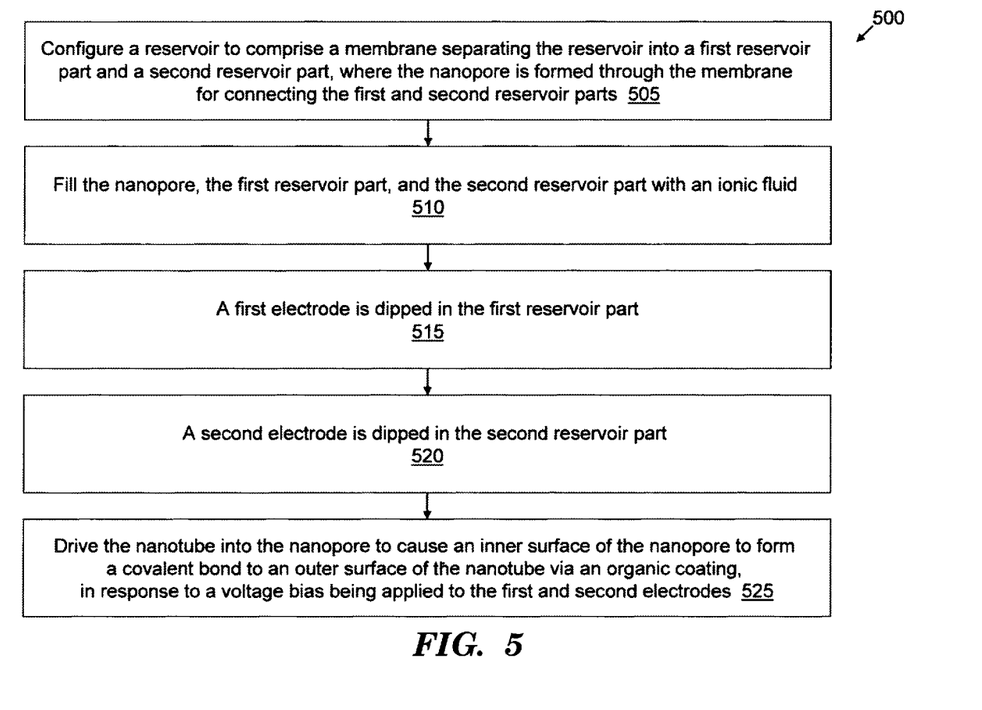
FIG. 5 is a method for embedding a nanotube inside a nanopore according to an exemplary embodiment.

FIG. 5 illustrates a method 500 for embedding a nanotube in a nanopore in accordance with an exemplary embodiment. Reference can be made to FIGS. 1, 2A, 2B, 2C, 3A, 3B, 3C, 4A, 4B, and 4C.

A reservoir (e.g., reservoir 104, 208) is configured to include a membrane (e.g., membrane 150, 250) separating the reservoir into a first reservoir part (e.g., reservoir part 105, 210) and a second reservoir part (e.g., reservoir part 106, 209) in which the nanopore (e.g., nanopore 103, 207) is formed through the membrane for connecting the first and second reservoir parts at block 505.

The nanopore, the first reservoir part, and the second reservoir part are filled with an ionic fluid (e.g., ionic fluid 107, 211) at block 510. A first electrode (e.g., electrode 110) is dipped in the first reservoir part at block 515, and a second electrode (e.g., electrode 111) is dipped in the second reservoir part at block 520.

At block 525, the nanotube is driven into the nanopore to cause an inner surface of the nanopore (e.g., nanopore 103, 207) to form a covalent bond to an outer surface of the nanotube (e.g., nanotube 102, 204) via an organic coating (e.g., organic coating 205, 206, 215), in response to a voltage bias being applied (e.g., by the voltage source 109) to the first and second electrodes (e.g., electrodes 110 and 111). Also, the carbon nanotube 204 can be driven into the nanopore 207 by the difference in fluidic pressure on both sides of the membrane 250 applied by the positive and negative pressures of the fluidic pressure adjustment devices 280 and 285.

The inner surface of the nanopore 207 may be coated with the organic coating (e.g., organic coating 215 in FIG. 3A or organic coating 206 in FIG. 4A) to form the covalent bond to the outer surface of the nanotube 204. Also, the outer surface of the nanotube 204 may be coated with the organic coating 205 to form the covalent bond to the inner surface of the nanopore 207.

In one case, both the inner surface of the nanopore 207 and the outer surface of the nanotube 204 are coated with the organic coating (e.g., the organic coatings 205 and 206 may be the same material in FIGS. 4A, 4B, and 4C), such that the organic coating on the inner surface of the nanopore 207 and the organic coating on the outer surface of the nanotube 204 cause the covalent bond in response to the voltage source 109 driving the nanotube 204 into the nanopore 207.

In another case, the inner surface of the nanopore 207 is coated with the organic coating and the outer surface of the nanotube is coated with another organic coating (e.g., the organic coatings 205 and 206 may be different materials in FIGS. 4A, 4B, and 4C), such that the organic coating on the inner surface of the nanopore and the other organic coating on the outer surface of the nanotube cause the covalent bond in response to the voltage source 109 driving the nanotube into the nanopore.

The covalent bond via the organic coating causes the nanotube 102, 204 to be physically attached to the nanopore 103, 207 formed in the membrane 150, 250, and both sides (e.g., top and bottom) of the membrane 150, 250 are processed such that a height of the nanotube corresponds to a height of a layer (e.g., membrane part 202) of the membrane 250 as shown in FIGS. 2C, 3C, and 4C.

For explanatory purposes, various examples of the organic coatings 205, 206, and 215 are discussed below. It is understood that the chemical molecules of the organic coatings 205, 206, and 215 discussed below are not meant to be limited.

The organic coating 205 can be prepared by reaction of aryldiazonium salts with the carbon nanotube 204. In this reaction, the diazonium salts are reduced by electron transfer from the carbon nanotube 204 to diazonium salts and results in the expulsion of one molecule of nitrogen and formation of a carbon-carbon bond between aryl compound and the carbon nanotube 204. This is a widely used reaction for functionalization of carbon nanotubes with a variety of aryl compounds mainly because of the simplicity of the reaction and the wide range of arydiazonium salts available through their corresponding arylamines. The reaction of aryldiazonium salts with the carbon nanotube 204 takes place either in aqueous solution or an organic solvent like dichloroethane, chloroform, toluene, dimethylformamide, etc. The reaction of aryldiazonium salts with the carbon nanotube 204 is very fast (e.g., completed within a few minutes) and takes place at room temperature. The preferred, but not required, diazonium salts are those with an additional functionality which can form strong bonds with metal oxides or nitrides inside the nanopore 207. The additional functionality (to form strong bonds with metal oxides or nitrides inside the nanopore 207) can be chosen from carboxylic acids ($-CO_2H$), hydroxamic acids ($-CONHOH$), or phosphonic acids ($-PO_3H_2$).

In FIGS. 3A, 3B, and 3C, the organic coating 215 is a bifunctional compound/molecule in which one functionality is a diazonium salt and the other functionality can be chosen from hydroxamic acid or phosphonic acid. When the nanopore 207 with inside walls of metal oxide or metal nitride is immersed in a solution of this bifunctional compound/molecule, the inner surface of the nanopore 207 is coated with the self-assembled monolayer of this bifunctional compound/molecule through hydroxamic acid or phosphonic acid functionality and exposes the diazonium functional group; the diazonium functional group can react with the uncoated carbon nanotube 204 (as shown in FIGS. 3B and 3C) to form a covalent bond, therefore immobilizing the carbon nanotube 204 inside the nanopore 207.

In FIGS. 4A, 4B, and 4C, both the carbon nanotube 204 and nanopore 207 are coated with organic monolayers (i.e., organic coatings 205 and 206 respectively). In the case of the carbon nanotube 204, the organic coating 205 is achieved by reaction of the carbon nanotube 204 with bifunctional diazonium salts which have either alcohol or amine groups, and the organic coating 206 inside the nanopore 207 is a bifunctional molecule having a functional group which forms a bond inside the nanopore 207 wall (e.g., hydroxamic acid or phosphonic acid) and the second exposed functionality which forms a covalent bond through condensation with exposed functionality of the carbon nanotube 204 (e.g. carboxylic acid). For example, the nanopore 207 can be coated with 4-carboxybenzylphosphonic acid by immersion of the nanopore 207 in a dilute (1-5 mmolar) solution of the latter in water or alcohol. After rinsing with the same solvent, the inside of the nanopore 207 (the wall or portion of the nanopore wall must be of metal oxide or nitride) is coated with a self assembled monolayer of 4-carboxybenzylphosphonic acid in a way that phosphonic acid forms covalent bonds with metal oxide or nitride and exposes the carboxylic acid functionality. In the second step, the functionalized carbon nanotube 204 having an alcohol or amine functionality is pulled inside the nanopore 207 and with the aid of a dehydrating agent (which must be present in the salt solution) the two functionalities of carboxylic acid and alcohol (or amine) undergo dehydration to form carboxylic ester (or carboxamide) resulting in immobilization of carbon nanotube 204. An example of the dehydrating agent (which is also water soluble and can be used in this environment) is N-(3-dimethylaminopropyl)-N'-ethylcarbodiimide hydrochloride. In FIGS. 4B and 4C, after the organic coating 205 and 206 react with each other to form an ester or amide, the joined coatings are designated as 270.

For the reaction (corresponding to FIGS. 2A, 2B, and 2C) when the nanopore 207 is uncoated and the carbon nanotube 204 is coated (with organic coating 205 as discussed above), the organic coating 205 is achieved by the reaction of a bifunctional aryldiazonium salt. For example, 4-aminobenzylphosphonic acid is treated with nitrosonium tetrafluoroborate to form corresponding diazonium salt. A solution of this diazonium salt is added to an aqueous dispersion of carbon nanotubes containing small (0.1-1%) amount of surfactant (e.g., sodium dodecylsulfate or sodium cholate). After stirring at room temperature for 30 minutes, the carbon nanotube 204 is functionalized with benzylphsophonic acid. An aqueous solution of the functionalized carbon nanotube 204 obtained above containing 0.1% anionic surfactant is pulled into nanopore 207 (as shown in FIGS. 2A, 2B, 2C) where the phosphonic acid functionality reacts with the surface of metal oxide (or nitride) inside the nanopore 207 to form a covalent bond.

For the reaction (corresponding to FIGS. 3A, 3B, and 3C) when the nanopore 207 is coated (with organic coating 215) and the carbon nanotube 204 is uncoated, the inside of the nanopore 207 is coated (organic coating 215) with bifunctional arylamine, e.g., 4-aminophenylhydroxamic acid by immersion of the nanopore 207 in a dilute (1-5 mmolar) solution of the amine in ethanol. After sometime (e.g., 1-24 hours, preferably 1-2 hours) the substrate (forming the nanopore 207) is removed and rinsed with ethanol. This step results in self assembly of 4-aminophenylhydroxamic acid on the inside wall of nanopore 207 by formation of covalent bonds through hydroxamic acid functionality with metal oxide (or nitride) of the nanopore 207 and exposing arylamine functionality. Next, the coated nanopore 207 is treated with a dilute solution of nitrosonium ion (e.g., a solution of nitrosonium tetrafluoroborate or dilute solution of sodium nitrite in dilute hydrochloric acid) resulting in transformation of the amine group to diazonium salt. In the last step, the uncoated carbon nanotube 204 in salt solution is pulled into the coated nanopore 207 which will react with diazonium functionality of the self assembled monolayer and form carbon-carbon bond to immobilize the carbon nanotube 204 inside the nanopore 207.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one ore more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the exemplary embodiments of the invention have been described, it will be understood that those skilled in the art, both now and in the future, may make various improvements and enhancements which fall within the scope of the claims which follow. These claims should be construed to maintain the proper protection for the invention first described.

What is claimed is:

1. An apparatus for embedding a nanotube in a nanopore, the apparatus comprising:
    a membrane separating a reservoir into a first reservoir part and a second reservoir part, the nanopore being formed through the membrane for connecting the first and second reservoir parts;
    an ionic fluid filling the nanopore, the first reservoir part, and the second reservoir part;
    a first electrode dipped in the first reservoir part;
    a second electrode dipped in the second reservoir part;
    the nanotube embedded in the nanopore as a smooth inner surface for the nanopore in which an outer surface of the nanotube fits an inner surface of the nanopore from top to bottom;
    the inner surface of the nanopore forms a covalent bond to the outer surface of the nanotube via an organic coating when the nanotube is driven into the nanopore by a voltage bias being applied to the first and second electrodes.

2. The apparatus of claim 1, wherein the inner surface of the nanopore is coated with the organic coating to form the covalent bond to the outer surface of the nanotube.

3. The apparatus of claim 1, wherein the outer surface of the nanotube is coated with the organic coating to form the covalent bond to the inner surface of the nanopore.

4. The apparatus of claim 1, wherein the inner surface of the nanopore is coated with the organic coating and the outer surface of the nanotube is coated with the organic coating; and
    wherein the organic coating on the inner surface of the nanopore and the organic coating on the outer surface of the nanotube cause the covalent bond in response to driving the nanotube into the nanopore.

5. The apparatus of claim 1, wherein the inner surface of the nanopore is coated with the organic coating and the outer surface of the nanotube is coated with another organic coating; and
    wherein the organic coating on the inner surface of the nanopore and the another organic coating on the outer surface of the nanotube causes the covalent bond in response to driving the nanotube into the nanopore.

6. The apparatus of claim 1, wherein the covalent bond via the organic coating causes the nanotube to be attached to the nanopore in the membrane.

7. The apparatus of claim 6, wherein both sides of the membrane are processed such that a height of the nanotube corresponds to a height of a layer of the membrane.

8. A system for embedding a nanotube in a nanopore, the system comprising:
an apparatus comprising:
a membrane separating a reservoir into a first reservoir part and a second reservoir part, the nanopore being formed through the membrane for connecting the first and second reservoir parts;
an ionic fluid filling the nanopore, the first reservoir part, and the second reservoir part;
a first electrode dipped in the first reservoir part;
a second electrode dipped in the second reservoir part; and
the nanotube embedded in the nanopore as a smooth inner surface for the nanopore in which an outer surface of the nanotube fits an inner surface of the nanopore from top to bottom within the nanotube; and
a voltage source configured to drive the nanotube into the nanopore so that the outer surface of the nanotube is in contact with the inner surface of the nanopore to form a covalent bond via an organic coating.

9. The system of claim 8, wherein the inner surface of the nanopore is coated with the organic coating to form the covalent bond to the outer surface of the nanotube.

10. The system of claim 8, wherein the outer surface of the nanotube is coated with the organic coating to form the covalent bond to the inner surface of the nanopore.

11. The system of claim 8, wherein the inner surface of the nanopore is coated with the organic coating and the outer surface of the nanotube is coated with the organic coating; and
wherein the organic coating on the inner surface of the nanopore and the organic coating on the outer surface of the nanotube form the covalent bond while the nanotube is driven into the nanopore.

12. The system of claim 8, wherein the inner surface of the nanopore is coated with the organic coating and the outer surface of the nanotube is coated with another organic coating; and
wherein the organic coating on the inner surface of the nanopore and the another organic coating on the outer surface of the nanotube form the a covalent bond while the nanotube is driven into the nanopore.

13. The system of claim 8, wherein the covalent bond via the organic coating causes the nanotube to be attached to the nanopore in the membrane.

14. The system of claim 13, wherein both sides of the membrane are processed such that a height of the nanotube corresponds to a height of a layer of the membrane.

15. An apparatus for embedding a nanotube in a nanopore, the apparatus comprising:
a membrane separating a reservoir into a first reservoir part and a second reservoir part, the nanopore being formed through the membrane for connecting the first and second reservoir parts;
an ionic fluid filling the nanopore, the first reservoir part, and the second reservoir part;
a first electrode dipped in the first reservoir part;
a second electrode dipped in the second reservoir part; and
the nanotube embedded in the nanopore as a smooth inner surface for the nanopore in which an outer surface of the nanotube fits an inner surface of the nanopore from top to bottom within the nanotube;
wherein the nanotube is driven into the nanopore by a difference in fluidic pressure on two sides of the membrane, which causes the inner surface of the nanopore to form a covalent bond to the outer surface of the nanotube via an organic coating.

16. The apparatus of claim 15, wherein one side of the membrane has a positive fluidic pressure and another side of the membrane has a negative fluidic pressure.

* * * * *